United States Patent [19]

Beaucamp et al.

[11] 4,343,903

[45] Aug. 10, 1982

[54] PROCESS FOR OBTAINING CHOLESTEROL ESTERASE FROM MICRO-ORGANISMS

[75] Inventors: Klaus Beaucamp; Michael Nelboeck; Helmgard Gauhl; Hans Seidel, all of Tutzing; Wolfgang Gruber, Tutzing-Unterzeismering; Herwig Brunner, Weilheim, all of Fed. Rep. of Germany

[73] Assignee: Boehringer Mannheim GmbH, Mannheim-Waldhof, Fed. Rep. of Germany

[21] Appl. No.: 175,808

[22] Filed: Aug. 6, 1980

[30] Foreign Application Priority Data

Aug. 20, 1979 [DE] Fed. Rep. of Germany ....... 2933646

[51] Int. Cl.$^3$ .............................................. C12N 9/18
[52] U.S. Cl. ..................................... 435/197; 435/244

[58] Field of Search ................. 435/197, 196, 11, 244; 426/662

[56] References Cited

U.S. PATENT DOCUMENTS 3,925,164 12/1975 Beaucamp et al. ............. 435/197 X
4,011,138  3/1977 Terada et al. ........................ 435/197
4,052,263 10/1977 Masurekar et al. ................. 435/197

*Primary Examiner*—Lionel M. Shapiro
*Attorney, Agent, or Firm*—Felfe & Lynch

[57] ABSTRACT

The present invention provides a process for obtaining cholesterol esterase from micro-organisms, wherein a micro-organism capable of cholesterol esterase formation is cultured in an appropriate nutrient medium in the presence of lecithin as inducer and the enzyme is obtained from the culture medium and/or from the cells.

5 Claims, No Drawings

PROCESS FOR OBTAINING CHOLESTEROL ESTERASE FROM MICRO-ORGANISMS

The present invention is concerned with a process for obtaining cholesterol esterase from micro-organisms.

Cholesterol esterase has played an important role in clinical and biochemical analysis ever since processes have been developed for the enzymatic determination of cholesterol. Since a large part of the cholesterol in biological material is present in the form of esters, the joint use of cholesterol esterase and cholesteroloxidizing enzymes, such as cholesterol oxidase or cholesterol dehydrogenase, make possible a completely enzymatic determination of cholesterol esters. This is known from Federal Republic of Germany Pat. No. 2,264,847. The enzyme from micro-organisms has proved to be especially useful for determination processes involving the use of cholesterol esterase (see Federal Republic of Germany Pat. No. 2,506,712). However, a disadvantage of the previously discovered micro-organisms with a content of cholesterol esterase which is sufficiently great to make a working up thereof worthwhile is the relatively low yields of enzyme activities which are obtained.

In the case of the known processes, culturing is normally carried out in a nutrient medium which contains an inducer. By "inducer", there is to be understood a substance which stimulates the micro-organism to produce the desired enzyme at all or to produce it in amounts greater than those produced without the use of an inducer. Normally, micro-organisms do not require cholesterol esterase since sufficient other sources of nutrition are available to them and the formation of an unnecessary enzyme is uneconomic for the cells. Therefore, inducers consist of cholesterol esters or of chemically similar compounds.

Surprisingly, we have now found that in the case of the use of a particular inducer which chemically differs considerably from cholesterol esters, very considerably higher activities can be achieved than was previously possible.

Thus, according to the present invention, there is provided a process for obtaining cholesterol esterase from micro-organisms, wherein a micro-organism capable of cholesterol esterase formation is cultured in an appropriate nutrient medium in the presence of lecithin as inducer and the enzyme is obtained from the culture medium and/or from the cells.

The inducer used according to the present invention is preferably also used as a source of carbon and especially as the sole source of carbon. However, it is also possible to add separate sources of carbon, for example maize steep liquor, peptones and yeast extracts, as well as, but less preferably, sugars or polyalcohols, such as glycerol. Amongst the various lecithins, soya lecithin has proved to be especially suitable but other kinds of lecithin, such as egg lecithin or brain lecithin, also gave very good results.

Generally speaking, the amount of lecithin used is from about 0.1 to 5% by weight, referred to the volume of the nutrient medium. When using lecithin as inducer and sole source of carbon, especially good results have been obtained with the use of amounts of from 0.5 to 2% by weight.

For the process according to the present invention, in principle there can be used all micro-organisms which are able to produce cholesterol esterase in an amount which makes working up thereof worthwhile. Large numbers of such micro-organisms are known. Thus, for example, the following micro-organisms can be used:

| | |
|---|---|
| Candida rugosa | ATCC 14830 |
| Rhizopus spec. | DSM 695 |
| Aspergillus spec. | DSM 698 |
| Streptomyces aureoverticillium | DSM 40080 |
| Streptomyces griseomycini | DSM 40159 |
| Streptomyces cyaneoluscatus | DSM 40148 |
| Streptomyces longisporus-fl. | DSM 40165 |
| Streptomyces roseolus | DSM 40174 |
| Streptomyces toxytricini | DSM 40178 |
| Streptomyces variabilis | DSM 40179 |
| Streptomyces spec. | DSM 687 |
| Streptomyces autotrophicus | DSM 40011 |
| Streptomyces canescens | DSM 40528 |
| Streptomyces chartreusis | DSM 40085 |
| Streptomyces michiganensis | DSM 40015 |
| Streptomyces murinus | DSM 40091 |
| Streptomyces hachijoensis | DSM 40114 |
| Streptomyces caelestes | DSM 40084 |
| Streptomyces tendae | DSM 40101 |
| Nocardia rubra | DSM 43008 |
| Candida mycoderma | DSM 688 |
| Candida albicans | DSM 689 |
| Candida albicans | DSM 690 |
| Candida albicans | DSM 691 |
| Candida spec. | DSM 692 |
| Cunninghamella elegans | DSM 693 |
| Mucor mucedo | DSM 694 |
| Penicillium spec. | DSM 696 |
| Aspergillus spec. | DSM 697 |
| Pseudomonas fluorescens | ATCC 31156 |
| Pseudomonas fluorescens | IAM 1051 |
| Pseudomonas fluorescens | ATCC 948 |
| Pseudomonas fluorescens | KY 4032 |
| Pseudomonas fluorescens | IFO 3081 |
| Pseudomonas spec. | IAM 18002 and 18001 |

Pseudomonas spec. DSM 1280 and 1281 are especially preferred.

An especially preferred nutrient medium, which is particularly suitable for the Pseudomonas types, also contains the conventionally added salts and trace elements and, by the addition of an appropriate buffer, should be adjusted to a pH value of from about 5 to 9 and preferably of 6 to 8. The buffer used is preferably a phosphate buffer. Furthermore, the nutrient medium preferably also contains ammonium, chlorine, iron, copper, zinc, magnesium and calcium ions, apart from the alkali metal ions of the phosphate buffer. Phosphate is thereby preferably present in a concentration of from 0.4 to 2% by weight but can also be added in higher or lower concentrations.

According to the present invention, an especially preferred nutrient medium has the following approximate composition, referred to 1 liter of liquid:

5 to 10 g. and preferably 6 to 8 g. disodium monohydrogen phosphate dihydrate,
1 to 5 g. and preferably 2 to 4 g. monopotassium dihydrogen phosphate,
0.2 to 2 g. and preferably 0.8 to 1.2 g. ammonium chloride,
0.01 to 0.1 g. and preferably 0.3 to 0.7 g. sodium chloride,
0.01 to 1 ml. 1% ferric chloride solution,
0.01 to 1 ml. 0.2% cupric chloride solution,
0.01 to 1 ml. 1% zinc sulphate solution,
0.1 to 10 ml. 10% calcium chloride solution,
1 to 20 ml. and preferably 3 to 10 ml. 12% magnesium sulphate solution, 0.1 to 5% by weight and preferably 0.5 to 2% by weight soya lecithin.

The culturing of the especially preferred micro-organisms is carried out in the above nutrient media under aerobic conditions. There can be used not only a shaken culture but also an aerated submersion culture. The temperature used can be from about 15° to about 45° C. and is preferably from 25° to 35° C. In general, maximum enzyme yields are obtained after a culture period of only 1 to 2 days.

The cholesterol esterase can occur not only in the culture medium but also in the cells. By means of the addition of surface-active agents and especially of non-ionic agents, which are preferably of the polyoxyethylene ester and ether type with alkyl and aralkyl radicals, in the case of many micro-organisms, the partitioning between the culture broth and the cells can be influenced, in the sense of increasing the extra-cellular activity at the expense of the intracellular activity; however, when using ionic surface-active agents, a change of the partitioning sometimes takes place in the opposite direction.

When culturing is finished, the cholesterol esterase is isolated from the cell mass and/or from the culture filtrate according to conventional methods and possibly purified. However, for many purposes, even the unpurified crude product can be used which consists essentially only of the digested cell mass. For digestion, there can be used the methods known for this purpose which do not need to be described here in detail. From the culture filtrate, as well as from the digested cell mass, after separation of insoluble components, the enzyme can be precipitated with conventional precipitation agents, for example salts, such as ammonium sulphate, or organic solvents, such as acetone or alcohols, and then, if desired, further purified by conventional fractionation methods, such as chromatography and precipitation.

The following Examples are given for the purpose of illustrating the present invention:

EXAMPLE 1

Pseudomonas spec. DSM 1280, taken from a deep cooled ampoule on tilted tubelets, is aerobically (shaking flask) pre-cultured in the main culture medium for 2 days at 30° C. and then inoculated in an amount of 10% into a medium which, per liter, has the following composition:

7 g. disodium monohydrogen phosphate dihydrate,
3 g. monopotassium dihydrogen phosphate,
1 g. ammonium chloride,
0.05 g. sodium chloride,
0.1 ml. 1% ferric chloride solution,
0.1 ml. 0.2% cupric chloride solution,
0.1 ml. 1% zinc sulphate solution,
1.0 ml. 10% calcium chloride solution,
5.0 ml. 12% magnesium sulphate solution,
1.5% soya lecithin,
pH 7.0.

Culturing is carried out aerobically at 30° C. in a shaking flask. After 1 to 3 days, activities of about 15,000 U/liter are obtained (supernatant and biomass; substrate:cholesteryl oleate).

About the same yields are obtained when, under the same conditions, instead of Pseudomonas spec. DSM 1280, there is used Pseudomonas spec. DSM 1281.

EXAMPLE 2

The insoluble cell mass is centrifuged off from a culture solution obtained according to Example 1 and used for the determination of cholesterol esters. The determination is carried out according to the following reaction equations:

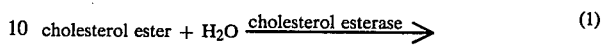

$$\text{cholesterol ester} + H_2O \xrightarrow{\text{cholesterol esterase}} \text{cholesterol} + \text{fatty acid} \quad (1)$$

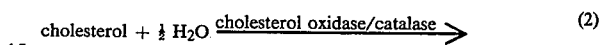

$$\text{cholesterol} + \tfrac{1}{2} H_2O \xrightarrow{\text{cholesterol oxidase/catalase}} \text{cholestenone} + H_2O_2 \quad (2)$$

(Measurement of cholestenone formation at 240 nm).

The following solutions are used for the measurement:

(1) phosphate buffer, 0.5 M, pH 7.5; 0.4% thesit,
(2) cholesterol oleate, c=4 in thesit/dioxan (1:1 v/v),
(3) hydrogen peroxide about 0.6 M (5 ml. perhydrol/100 ml.),
(4) catalase (0.01 mg. protein/ml.),
(5) cholesterol oxidase (at least 50 U/ml.),
(6) culture solution (in the case of about 5000 U/liter diluted 1:5 with water, 0.01 ml. per test).

For carrying out the measurement, 2.95 ml. of solution 1) are mixed with 0.02 ml. of Solution 3). After 5 minutes, 0.01 ml. of Solution 6) and 0.02 ml. of Solution 5) are added thereto and, after 1 minute, the reaction is started by the addition of 0.1 ml. of Solution 2).

The calculation is carried out as follows:

$$\frac{3.12 \times 5 \times 1000}{15.5 \times 0.01} \times \Delta E/\text{min.} = \text{U/liter culture solution.}$$

EXAMPLE 3

*Candida rugosa* ATCC 14830, taken from a deep cooled ampoule on tilted tubelets, is inoculated into a culture medium of the following composition and cultured aerobically (shaking flask 20/100) for 48 hours at 28° to 30° C. A medium is then inoculated with 10% of inoculum which, per liter, has the following composition:

20 g. soya meal GeFu 988 SUP
20 g. soluble starch
5 g. dipotassium monohydrogen phosphate trihydrate
1 g. magnesium sulphate heptahydrate
1 g. ammonium sulphate
1.5 g. soya lecithin
pH 6.6 to 6.8.

Culturing is carried out aerobically at about 28° C. After 3 to 4 days, activities of 1500 to 2000 U/liter are obtained (supernatant; test substrate:cholesteryl oleate).

It will be understood that the specification and examples are illustrative but not limitative of the present invention and that other embodiments within the spirit and scope of the invention will suggest themselves to those skilled in the art.

What is claimed is:

1. Process for obtaining cholesterol esterase from micro-organisms, which process comprises culturing a micro-organism capable of cholesterol esterase formation in a nutrient medium, in the presence of lecithin as an inducer, and then obtaining the enzyme from the culture medium or the cells.

2. Process as claimed in claim 1 wherein soya lecithin is used as the inducer.

3. Process as claimed in claim 1 wherein culturing is carried out in the presence of about 0.1 to 5% by weight of the inducer.

4. Process as claimed as claimed in claim 3 wherein culturing is carried out in the presence of from 0.5 to 2% by weight of lecithin.

5. Process as claimed in claim 1 wherein 0.4 to 2% by weight of phosphate is added to the medium.

* * * * *